United States Patent [19]

Moeller

[11] Patent Number: 4,706,897
[45] Date of Patent: Nov. 17, 1987

[54] APPARATUS FOR COMMINUTING BONE

[75] Inventor: Rudolph H. Moeller, Royal Palm Beach, Fla.

[73] Assignee: BioDynamic Technologies Inc., Pompano Beach, Fla.

[21] Appl. No.: 926,440

[22] Filed: Oct. 29, 1986

[51] Int. Cl.⁴ ............................................. B02L 18/22
[52] U.S. Cl. .................... 241/37.5; 241/100; 241/280; 241/285 A
[58] Field of Search ................ 241/32, 37.5, 100, 280, 241/281, 285 R, 285 A

[56]  References Cited
U.S. PATENT DOCUMENTS

| 2,680,282 | 6/1954 | Each et al. | 241/37.5 |
| 2,728,368 | 12/1955 | Van Guilder | 241/37.5 |
| 3,530,914 | 9/1970 | Lasar | 241/281 |
| 3,589,626 | 6/1971 | Saurer | 241/100 |

Primary Examiner—Timothy V. Eley
Attorney, Agent, or Firm—Larson and Taylor

[57]  ABSTRACT

An apparatus for comminuting homogeneous or autogeneous bone fragments into substantially homogeneous particles for use in bone grafting wherein a housing is provided having separate compartments for a motor and a comminuter driven by the motor. A chute and ram are provided to feed bone fragments into contact with the comminuter and the comminuted particles are collected in a removable tray. The compartment housing the comminuter may be readily disassembled for cleaning and, when so disassembled, the motor is vented to atmosphere to prevent operation. The resultant comminuter bone particles are collected in a removable tray below the comminuter.

6 Claims, 9 Drawing Figures

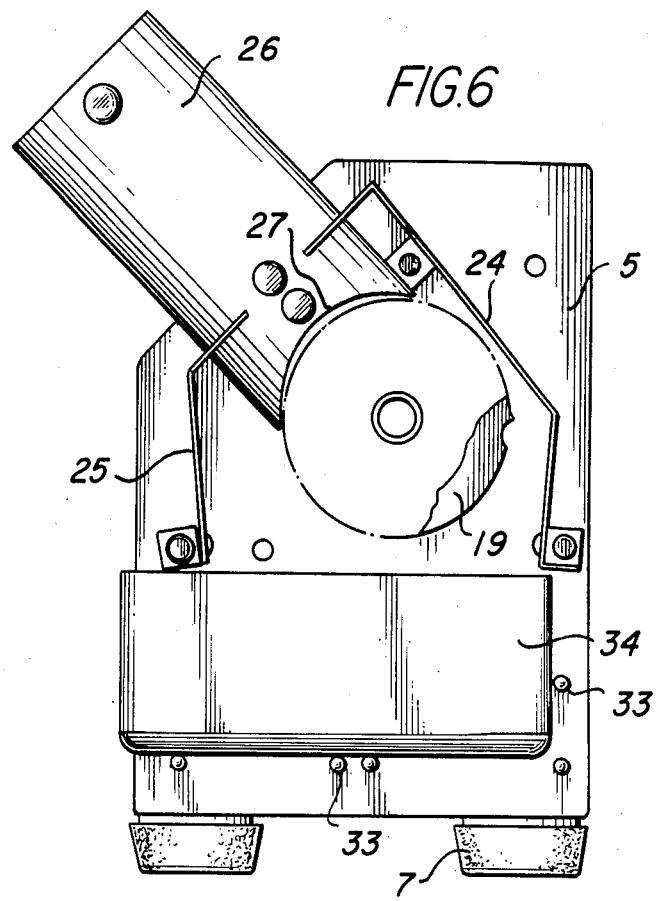
FIG.6
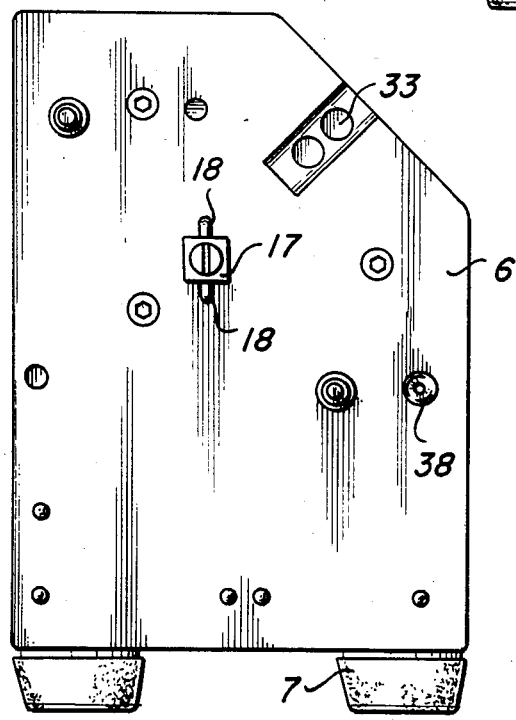
FIG.7
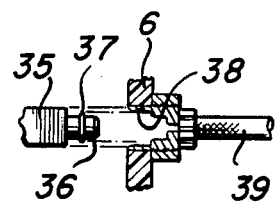
FIG.8
FIG.9

APPARATUS FOR COMMINUTING BONE

FIELD OF THE INVENTION

The present invention relates to an apparatus for comminuting bone into substantially homogeneous particles useful for bone grafting.

BACKGROUND OF THE INVENTION

Finely comminuted bone graft is important to successful total joint replacement especially for porous coated implants, spinal fusions and repair of defects caused by trauma. Therefore, it is necessary to have an apparatus which will comminute homogeneous or autogeneous bone into substantially homogeneous particles in a sterile environment.

One such known prior art apparatus includes a rotating cutter which is similar to a drill bit and a hopper into which bone fragments are placed. The operator grasps a handle which brings a compression plate into contact with the bone fragments. The compression plate pushes the bone fragments in the hopper into contact with the cutter. The bone fragments are milled into particles and collected in a tray below the cutter. The cutter may be powered by an electric motor or an air powered motor. This apparatus however, is not entirely safe to operate. The housing does not completely encase the cutter or motor making it possible to injure the operator. Additionally, the cutting blade may be operated even when the unit is partially disassembled. This is particularly dangerous since any such apparatus must be disassembled and reassembled after each use in order to clean and sterilize it.

Another prior art bone comminuting apparatus includes an air powered motor and a rotating cutting blade. This model includes a housing which completely encloses the motor and cutting blade. There is a generally horizontal chute into which bone pieces are placed prior to grinding. A push rod is used to move the bone pieces into the cutting chamber where they are comminuted. This unit does not provide an automatic shutoff to prevent operation of the cutter when the unit is disassembled for cleaning and sterilization.

There exists a need in the art for a bone comminuting device that produces substantially homogeneous bone particles, which may be readily disassembled and which includes additional safety features to protect the user.

SUMMARY OF THE INVENTION

The present invention relates to an apparatus for use in comminuting bone to substantially homogeneous particles which comprises a housing which may be readily disassembled, a rotating comminuter attached to the inside of the housing in a manner which allows free rotation of the comminuter, a motor adapted to drive the comminuter attached to the inside of said housing and to the rotating comminuter, and a collecting tray releasably engaged inside the housing below the comminuter. There is also provided a chute which extends into the housing and is attached intermediate its length to the housing, the chute having a first open end in close proximity to the comminufer, and a second open end outside the housing. A ram fits inside the chute and extends the length thereof. The ram is adapted to force bone into contact with the comminuter. There is also provided a means for automatically shutting off the motor when the housing is disassembled.

It is the primary object of the present invention to provide a safe and convenient apparatus for comminuting bone fragments into substantially homogeneous particles.

It is a further object of the present invention to provide a bone comminuting apparatus which may be easily and quickly disassembled for cleaning and sterilization.

It is a still further object of the present invention to provide a bone comminuting apparatus which includes safety features which prevent actuation of the comminuter when the housing is disassembled.

These and other objects of the present invention will be apparent from the detailed description to follow.

BRIEF DESCRIPTION OF THE DRAWINGS

FIG. 6 is a sectional view along the line 6—6 of FIG. 3;

FIG. 7 is a sectional view of the apparatus along the line 7—7 of FIG. 3; and

FIG. 8 is a view partially in section of the means for preventing operation of the motor when the apparatus is being disassembled.

FIG. 9 is an end elevational view of the rotor 19.

DETAILED DESCRIPTION OF THE PREFERRED EMBODIMENT

Figure 1:
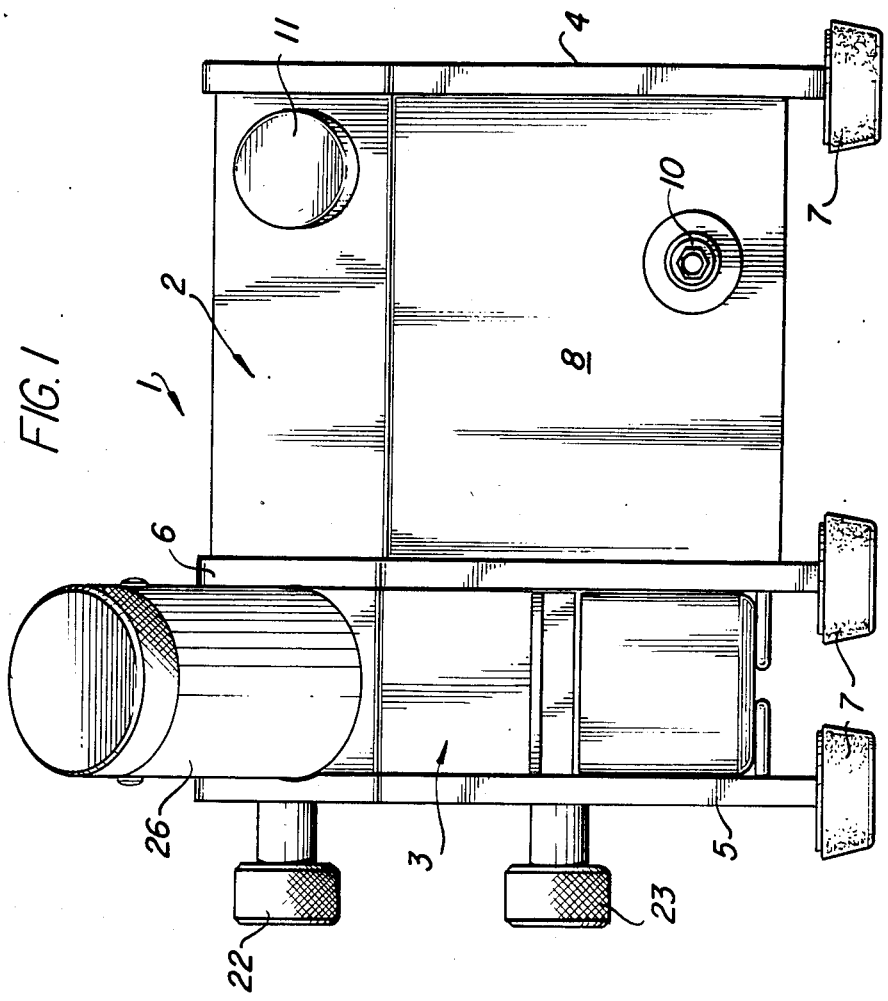
FIG. 1 is a side elevation of the apparatus according to the present invention.

The preferred embodiment of the presently disclosed bone comminuting device comprises a housing 1 having a pair of compartments including a motor housing 2 and a compartment 3 which houses the mechanism for comminuting bone.

There are provided end plates 4 and 5 and an intermediate plate 6 which separates the compartments 2 and 3. The plates 4, 5 and 6 are provided with feet 7 which can be made of rubber or the like.

Figure 3:
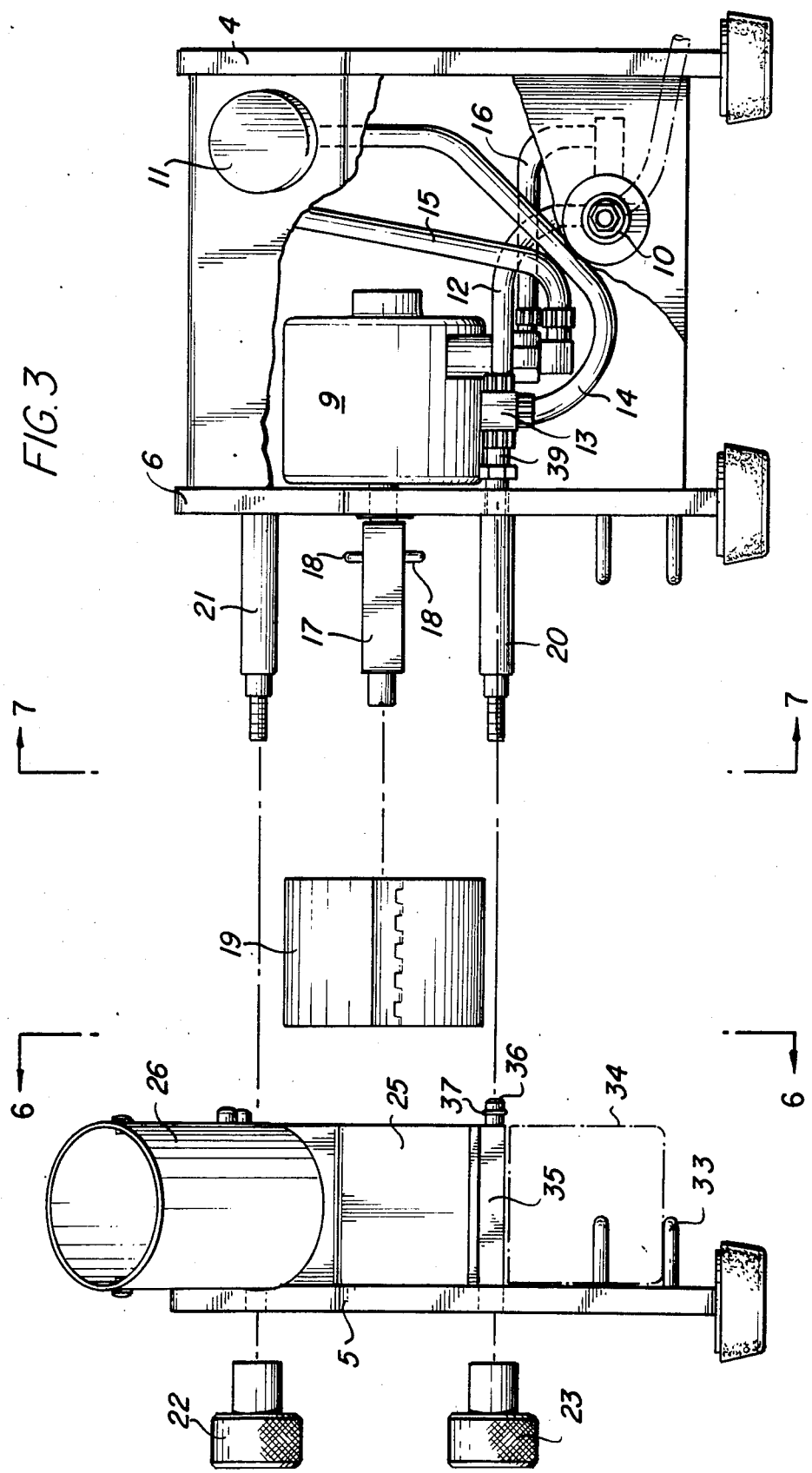
FIG. 3 is an exploded view of one end portion of the apparatus.

The motor housing 2 has a housing which is bent to conform to end plate 4 to completely encase the motor. As shown in FIG. 3 the motor 9 is mounted on the intermediate plate 6 and all of the elements essential for operation of the motor 9 are disposed within the compartment 2.

On the front face of the housing 2 there is provided a connecting opening 10 to which a tube connected to a source of compressed air or the like may be attached. An operating button 11 is also mounted on the front face of the motor compartment 2 and by depressing the operating button 11 compressed air is supplied to the turbine motor 9.

Figure 2:
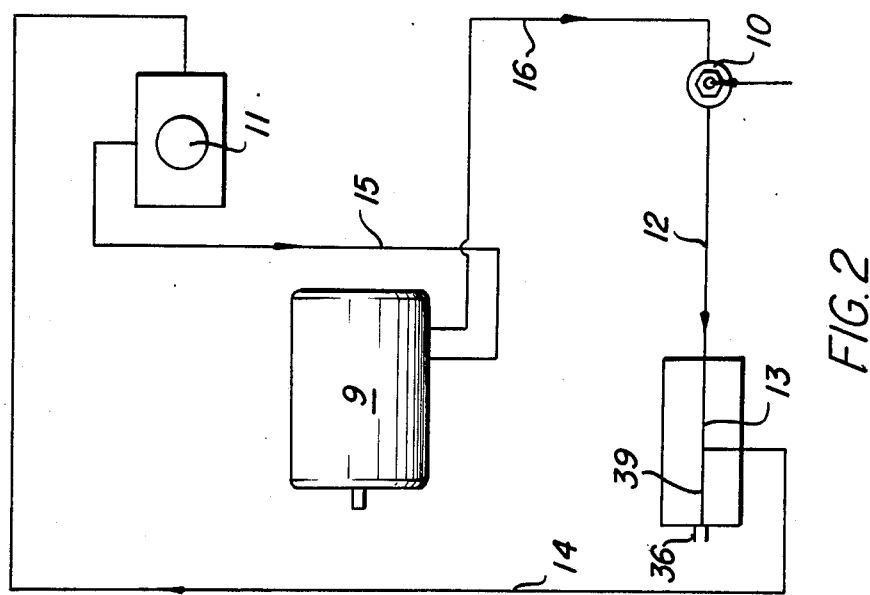
FIG. 2 is a diagrammatic sketch showing the pneumatic tubes for operation the motor.

In FIG. 2 there is shown a diagrammatic sketch of the pneumatic tube system which supplies gas to the motor 9 as well as returning the gas from the motor to the outlet. The tube 12 leading from the connecting orifice 10 is connected with a disconnect means 13 which will be described in detail hereinafter. The pneumatic tube 14 extending from the disconnect means 13 is connected to the off/on switch actuated by the operating button 11. Tube 15 leads from the operating off/on switch to the drive elements in the turbine motor 9. A return duct 16 extends from the motor to the connecting orifice 10 where a separate passageway is provided for the gas return thereto.

The motor 9 which is mounted on the intermediate plate 6 has an output shaft 17 extending through an aperture in plate 6. The output shaft 17 is provided with a pair of locating pins 18 thereon which provides a means for retaining the comminuter rotor 19 in properly aligned position on the rotor 17.

The comminuting compartment 3 is disposed between the end plate 5 and the intermediate plate 6. The end plate 5 is secured to the intermediate plate 6 by a pair of rods 20 and 21 which have threaded end portions. These rods 20 and 21 are secured to the intermediate plate 6 and extend through apertures in the end wall 5. There are provided knurlled knobs 22 and 23 which fit the end plate and parts mounted thereon to be readily disconnected from the intermediate plate 6.

As seen in FIG. 6 the end plate 5 has a pair of splash guards 24 and 25 secured thereto by any suitable means. The end portions of splash guards 24 and 25 are provided with semicircular cutouts to receive a chute 26 therebetween. As seen in FIG. 6 the end portion 27 of the chute 26 is shaped to conform to the periphery of the rotor 19.

Figure 4:
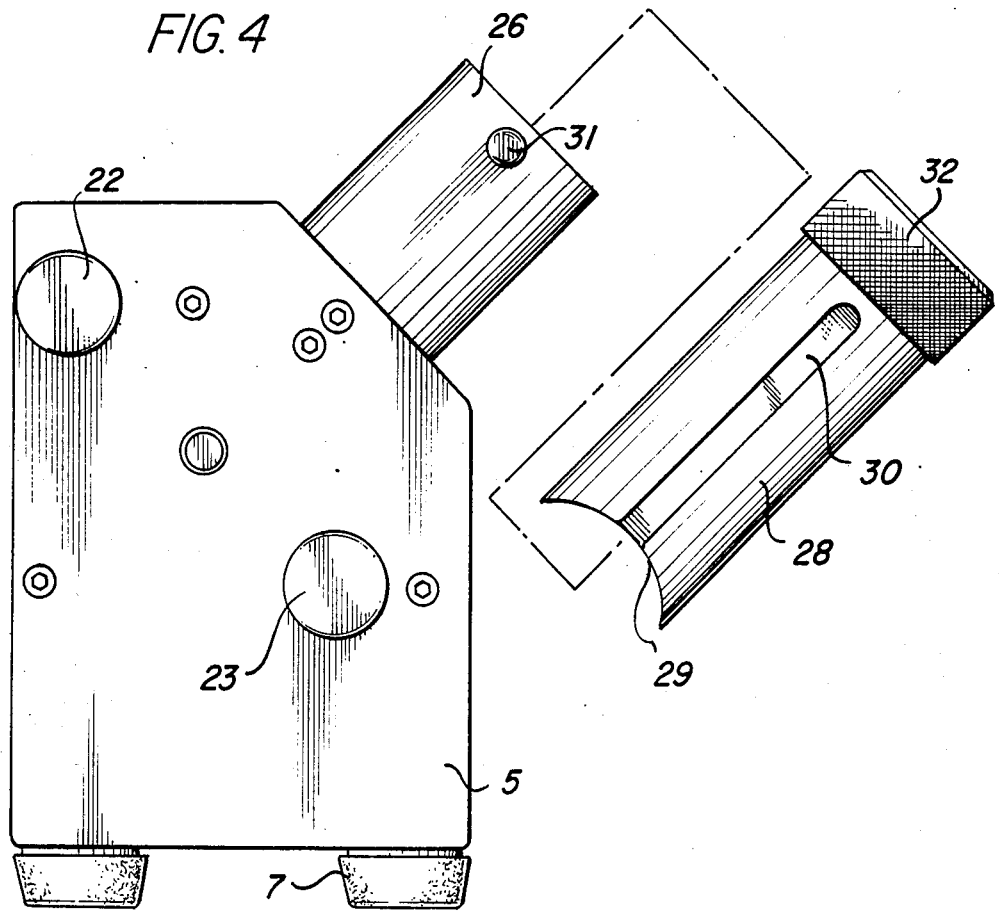
FIG. 4 is an end elevation view of the comminuting portion of the apparatus.
Figure 5:
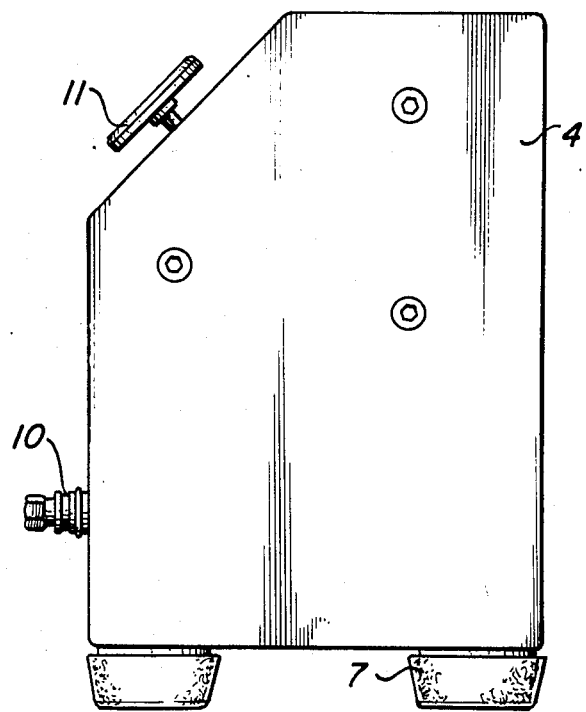
FIG. 5 is an opposite end elevation.

As shown in FIG. 4 there is provided a ram 28 which comprises a solid block of heavy metal having a semicircular end portion 29. The ram is provided with a pair of grooves 30, one groove being disposed on each side of the ram and being adapted to cooperate with a pair of pins 31 which extend inwardly from each side of the chute 26. At the outer end of the ram 28 there is provided a knurlled head 32 which is slightly larger than the ram. The head 32 will not fit within the chute 30 and will limit the inward movement of the ram 28 within the chute 26 so that it cannot come into contact with the comminuting rotor 19.

As can be seen in FIG. 6 there are provided a plurality of pins 33 which extend inwardly from the innerface of the end plate 5 to form a seat for a tray 34. It can be seen that the tray 34 fits beneath the splash guards 24 and 25 and is adapted to slide into and out of the comminuting compartment 3.

There is provided means for preventing the motor from being operated when the compartment 3 is detached from the motor compartment 2. A rod 35, as seen in FIG. 3, is fixed to end plate 5 and this rod is provided with a cylindrical end portion 36 having an O-ring 37 thereon. An opening 38 in intermediate plate 6 is sealed by the cylindrical end portion 36 of rod 35 with the O-ring 37 insuring that there is no leakage through aperture 38 when the comminuting compartment 3 is in operating position and the end plate 5 is secured to the rods 20 and 21. It can be seen in FIG. 3 that the disconnect device 13 has a passageway 39 leading to the aperture 38. Thus, when the end plate 5 is disconnected from rods 20 and 21, leaving the aperture 38 open any compressed gas which passes through the tube 14 will pass out through aperture 38. Even if the operating button 11 is accidentally depressed the motor 9 will not be operable unless the comminuting compartment 3 is in place.

The rotor is shown in FIG. 9 and it can be seen that a pair of cutting blades 40 are provided thereon. There is a longitudinal groove 41 extending along the face of the rotor 19 adjacent each cutting blade 40. Means is provided to replace the cutting blades or alternatively different rotors may be used to provide for fine or course cutting as desired.

In use the bone to be comminuted is placed within the chute 26 and the ram is inserted into the chute to force the bone into contact with the rotor 19. The ram is of sufficient weight to maintain the bone in contact with the rotor and without the need for additional pressure applied against the ram. By depressing the operating button 11 compressed gas is supplied to the turbine motor 9 to rotate the motor and cause the cutting blades 40 to fragment the bone. The bone chips collect within the tray 34 and the tray may be readily removed for subsequent use of the bone chips. After use the knurlled knobs 22 and 23 can be unscrewed by hand and the entire comminuting compartment may be removed from the rest of the assembly. When the comminuting compartment 3 is removed from the motor compartment 2, passageway 39 is open to atmosphere so that accidental actuation of the operating button 11 will cause the compressed air to pass through tube 14 and out to atmosphere rather than operating the motor 9.

Obviously many modifications and variations of the present invention are possible in light of the above teachings.

What is claimed as new and desired to be secured by Letters Patent is:

1. An apparatus for use in comminuting bone to substantially homogeneous particles which comprises,
    a first housing having a pair of end walls,
    a motor mounted in said first housing,
    an output shaft on said motor, said output shaft extending through one of said end walls,
    a second housing having a single end wall,
    a comminuter mounted on the output shaft of said motor and disposed within said second housing,
    a chute extending through said second housing and attached intermediate its length to said housing, said chute having a first open end in close proximity to said comminuter and a second open end outside said second housing,
    a ram disposed within said chute and extending the length thereof, said ram adapted to force bone into contact with said comminuter,
    a collecting tray releasably engaged inside said second housing below said comminuter,
    means for releasably attaching the singel end wall of said second housing to said one end wall of said first housing whereby said second housing with said chute, comminuter and collecting tray may be readily removed from said first housing for sterilization purposes.

2. An apparatus as claimed in claim 1 wherein said motor is air-powered.

3. An apparatus as claimed in claim 2 and further including means operatively connected to said motor for preventing operation of said motor when said second housing is removed.

4. An apparatus as claimed in claim 3 wherein said rotating comminuter comprises a substantially cylindrical surface having at least one blade-like protrusion thereon.

5. An apparatus as claimed in claim 4 wherein said chute includes a pair of guide pins attached on opposite sides of the inner surface of said chute, and said ram including a pair of slots adapted to engage said pins to guide said ram into said chute and to prevent rotation of said ram.

6. An apparatus as claimed in claim 1 wherein said chute protrudes from said housing at an angle of between 30 and 60 degrees from the horizontal.

* * * * *